United States Patent [19]

Hoeltje et al.

[11] Patent Number: 5,418,224
[45] Date of Patent: May 23, 1995

[54] 4,13-DIOXABICYCLO[8.2.1]TRIDECENONE COMPOUNDS AND PHARMACEUTICAL COMPOSITIONS CONTAINING THEM

[75] Inventors: Dagmar Hoeltje, Gronau; Ulf Preuschoff, Uelzen; Christian Eeckhout, Bad Pyrmont, all of Germany

[73] Assignee: Kali-Chemie Pharma GmbH, Hanover, Germany

[21] Appl. No.: 996,083

[22] Filed: Dec. 23, 1992

[30] Foreign Application Priority Data

Jan. 7, 1992 [DE] Germany ............ 42 00 145.5

[51] Int. Cl.6 .......... A61K 31/70; C07H 17/08
[52] U.S. Cl. ............ 514/28; 536/7.2; 536/18.1
[58] Field of Search .......... 536/7.2, 18.1; 514/28

[56] References Cited

U.S. PATENT DOCUMENTS 3,725,385  4/1973  Freiberg ............... 260/210
4,920,102  4/1990  Gidda et al. .......... 514/28
5,106,961  4/1992  Kirst et al. .......... 536/7.2

OTHER PUBLICATIONS

Tsuzuki et al., *Chem. Pharm Bull.*, vol. 37, No. 10, pp. 2687–2700 (1989).
Kibwage et al., *J. Antibiotics*, vol. 40, No. 1, pp. 1–6 (1987).
European Search Report, *The Hague*, completed Mar. 31, 1993.

*Primary Examiner*—Douglas W. Robinson
*Assistant Examiner*—Elli Peselev
*Attorney, Agent, or Firm*—Evenson, McKeown, Edwards & Lenahan

[57] ABSTRACT

Ring-contracted N-demethyl-N-isopropylerythromycin A derivatives with gastrointestinally effective motilin-agonistic properties, a method for preparing such compounds, and pharmaceutical compositions containing them.

2 Claims, No Drawings

4,13-DIOXABICYCLO[8.2.1]TRIDECENONE COMPOUNDS AND PHARMACEUTICAL COMPOSITIONS CONTAINING THEM

BACKGROUND OF THE INVENTION

The present invention relates to novel N-substituted [2R,3R(2R',3R'),6R,7S, 8S,9R,10R]-3-(2',3'-dihydroxypent-2'-yl)-7-[(2,6-dideoxy-3-C-methyl-3-0-methyl-α-L-ribo-hexopyranosyl)-oxy]-9- [(3,4,6-trideoxy-3-amino-β-D-xylo-hexopyranosyl)-oxy]-2,6,8,10,12-pentamethyl-4,13-dioxabicyclo[8.2.1]tridec-12-en-5-one compounds with motilin-agonistic properties and to the acid addition salts thereof and to pharmaceutical formulations containing these compounds and to process and intermediates for the preparation of these compounds. The compounds according to the invention are ring-contracted N-demethyl-N-isopropyl derivatives of erythromycin A.

In addition to its antibiotic effects, the antibiotic erythromycin A is known to also have gastrointestinal side effects which are undesired in antibiotics, inter alia a great increase in the contraction activity in the gastrointestinal region with gastric and intestinal cramps, nausea, vomiting and diarrhoea.

There have been several attempts to modify erythromycin A to obtain derivatives in which the antibiotic effect is virtually eliminated but an effect influencing the motility of the gastrointestinal tract is obtained. U.S. Pat. No. 4,920,102 discloses pharmaceutical compositions which contain as gastroprokinetic active substance a ring-contracted erythromycin A derivative or a quaternary salt thereof and which enhance gastric motility by cholinergic mechanisms.

SUMMARY OF THE INVENTION

It is the object of the present invention to provide ring-contracted derivatives of erythromycin A which do not have antibiotic activity, but which do exhibit a beneficial effect on the motility of the gastrointestinal tract.

It is also an object of the invention to provide intermediate compounds and a process for producing ring-contracted derivatives of erythromycin A.

These and other objects of the invention are achieved by providing a [2R,3R(2R',3R'),6R,7S,8S,9R,10R]-3-(2',3'-dihydroxypent-2'-yl)-2,6,8,10,12-pentamethyl-4,13-dioxabicyclo[8.2.1]tridec-12-en-5-one compound corresponding to the formula I:

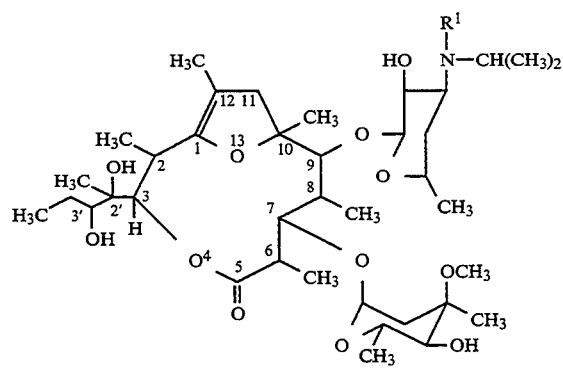

in which $R^1$ denotes methyl or hydrogen, or a stable and physiologically acceptable acid addition salt thereof.

In accordance with a further aspect of the invention, the objects are achieved by providing a process for preparing a [2R,3R(2R',3R'),6R,7S, 8S,9R,10R]-3-(2',3'-dihydroxypent-2'-yl)-2,6,8,10,12-pentamethyl-4,13-dioxabicyclo[8.2.1]tridec-12-en-5-one compound corresponding to the formula I:

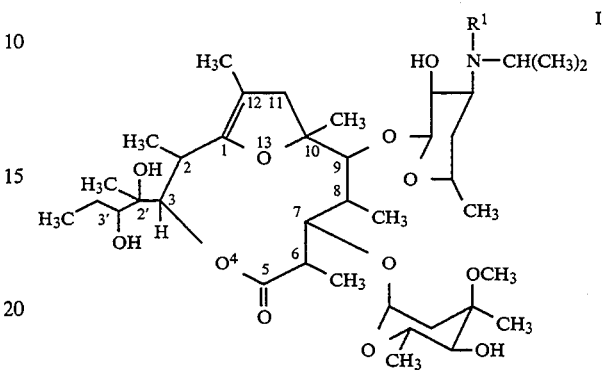

wherein $R^1$ represents methyl or hydrogen, or a stable and physiologically acceptable acid addition salt thereof, said process comprising: introducing an isopropyl radical into a [2R,3R(2R',3R'), 6R,7S,8S,9R,10R]-3-(2',3'-dihydroxypent-2'-yl)-2,6,8,10,12-pentamethyl-4,13-dioxabicyclo[8.2.1]tridec-12-en-5-one starting compound corresponding to the formula II:

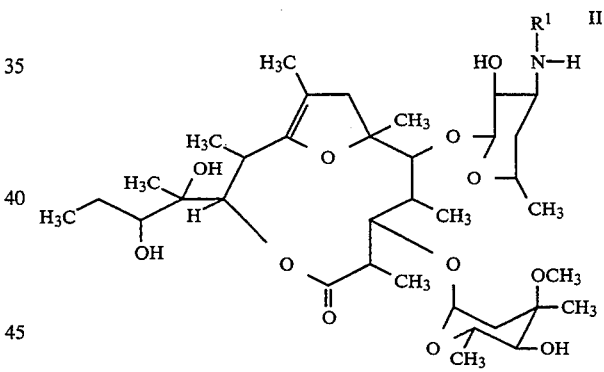

wherein $R^1$ has the above meaning.

DETAILED DESCRIPTION OF PREFERRED EMBODIMENTS

It has now been found that the novel ring-contracted N-demethyl-N-isopropyl derivatives of erythromycin A have selective motilin-agonistic properties and stimulate the motility of the gastrointestinal tract in a beneficial way and show effects enhancing the tone of the lower esophagus sphincter. Because of their activity profile, the compounds of the invention are suitable for treating motility disturbances in the gastrointestinal tract, and moreover they are distinguished by being well tolerated.

The present invention therefore relates to novel [2R,3R(2R',3R'),6R,7S,8S,9R,10R]-3-(2',3'-dihydroxypent-2'-yl)-2,6,8,10,12-pentamethyl-4,13-dioxabicyclo[8.2.1]tridec-12-en-5-one derivatives of the general formula I

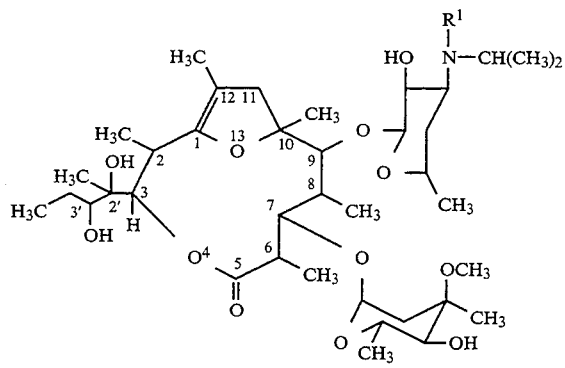

in which R¹ denotes methyl or hydrogen, and to the stable and physiologically acceptable acid addition salts thereof. The compound of formula I in which R¹ denotes methyl is particularly preferred.

The compounds of the formula I can be obtained by introducing an isopropyl radical in a known manner into [2R,3R(2R',3R'),6R,7S,8S,9R,10R]-3-(2',3'-dihydroxypent-2'-yl)-2,6,8,10,12-pentamethyl-4,13-dioxabicyclo[8.2.1]tridec-12-en-5-one compounds of the general formula II

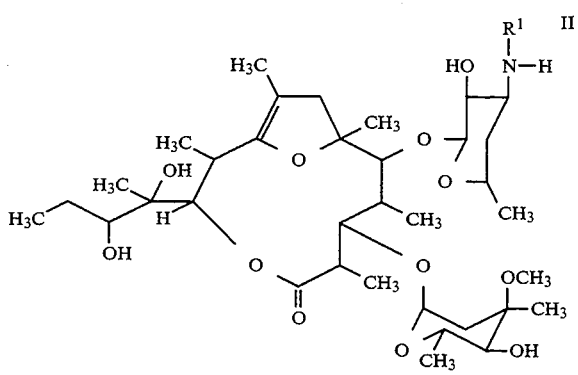

in which R¹ has the above meaning, and, if desired, introducing a methyl radical R¹ into the resulting compound of the formula I in which R¹ denotes hydrogen, or eliminating the methyl radical R¹ in the resulting compound of the formula I in which R¹ denotes methyl, and, if desired, converting free compounds of the formula I into the stable acid addition salts thereof, or converting the acid addition salts into the free compounds of the formula I.

To introduce the isopropyl radical, the compounds of the formula II can be alkylated in a known manner. The alkylation is preferably carried out as reductive alkylation in a known manner by reacting a compound of formula II with acetone under reducing conditions. For example, the compounds of the formula II can be reacted with acetone in the presence of a reducing agent, for example of a complex borohydride compound such as sodium cyanoborohydride, sodium triacetoxyborohydride or sodium borohydride. Optionally, the alkylation, particularly that of the compound of formula II in which R¹ denotes methyl, can also be carried out by reaction with an isopropyl halide, especially isopropyl iodide, or isopropyl sulfate or with an isopropyl sulfonate. The alkylation is advantageously carried out in an organic solvent which is inert under the reaction conditions. An excess of acetone can be used as solvent, for example, for the reductive alkylation. Also suitable as solvents are, furthermore, cyclic ethers such as tetrahydrofuran or dioxane, aromatic hydrocarbons such as toluene or else lower alcohols. The alkylation can be carried out at temperatures between room temperature and the boiling point of the solvent. The alkylation with an isopropyl derivative, for example an isopropyl halide such as isopropyl iodide, is advantageously carried out in the presence of a base such as, for example, an alkali metal carbonate or a tertiary organic amine.

The resulting compound of the formula I in which R¹ denotes hydrogen can, if desired, subsequently be alkylated in a known manner to give the corresponding N-methyl compound. The alkylation can take place in a known manner by reaction with a methyl halide or as reductive alkylation by reaction with formaldehyde under reducing conditions and can be carried out, for example, under the conditions described above for the alkylation of the compounds of formula II.

The methyl radical R¹ can, if desired, subsequently be eliminated from the compound of the formula I in which R¹ denotes methyl. The demethylation can be effected in a known manner by treating the compound with a halogen, especially iodine and/or bromine, in an inert solvent in the presence of a suitable base. Examples of suitable bases include alkali metal hydroxides and alkali metal salts of weak organic acids. The demethylation is preferably carried out in a weakly alkaline pH range of, preferably, below 9 in order to avoid hydrolysis side reactions.

The compounds of the formula I can be isolated from the reaction mixture and purified in a known manner. Acid addition salts can be converted in a conventional manner into the free bases, and the free bases can, if desired, be converted in a known manner into pharmacologically acceptable acid addition salts. To avoid hydrolysis side reactions, it is desirable to use only equivalent amounts of acids for the salt formation.

Examples of suitable pharmacologically acceptable acid addition salts of the compounds of the formula I are the salts thereof with inorganic acids, for example carbonic acid, hydrohalic acids, especially hydrochloric acid, or with organic acids, for example lower aliphatic mono- or dicarboxylic acids such as maleic acid, fumaric acid, lactic acid, tartaric acid or acetic acid.

The starting compounds of the formula II have not yet to date been described in the literature. According to the invention, the compounds of the formula II represent valuable intermediates for the preparation of pharmacologically active compounds, for example compounds of formula I.

The compounds of the formula II can be obtained starting from erythromycin A of the formula III

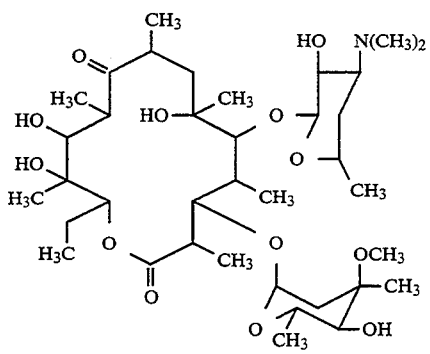

by known methods. Thus, erythromycin A can initially be mono- or didemethylated by reaction with halogen, preferably iodine, in an inert solvent in the presence of a suitable base in a known manner, for example by the process disclosed in U.S. Pat. No. 3,725,385. Examples of suitable bases include alkali metal hydroxides, alkali metal carbonates and alkali metal salts of weak carboxylic acids such as, for example, alkali metal acetates or propionates. From 1 to 5 equivalents of the halogen relative to the amount of erythromycin compound to be demethylated are preferably employed. The amount of the base is preferably chosen so that a pH in the range from 5 to 9 is assured, in order to avoid hydrolysis or alcoholysis side reactions. Suitable solvents include methanol, cyclic ethers such as dioxane or tetrahydrofuran, dimethylformamide or mixtures of the said solvents with water. The demethylation is advantageously carried out at temperatures between room temperature and 50° C. The reaction can be promoted by irradiation with light, for example light with a wavelength of above 290 nm from a low pressure mercury lamp with a filter made of quartz or heat-resistant glass (for example "Pyrex" TM). The reaction generates the monodemethylated or didemethylated product, mainly depending on the amount of halogen used. The monodemethylated product is preferentially obtained when one equivalent of halogen is used, and the didemethylated product is preferentially obtained when two or more equivalents of halogen are used. If desired, the preparation of the didemethylated product can also start from previously monodemethylated product.

The monodemethylated or didemethylated erythromycin A can be converted in a known manner by mild acid treatment into a corresponding mono- or didemethylated 8,9-anhydroerythromycin A 6,9-hemiketal of the general formula IV

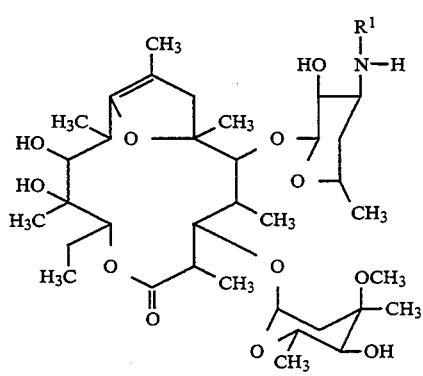

in which $R^1$ denotes hydrogen or methyl. The hemiketal formation can take place, for example, by treatment with glacial acetic acid or dilute mineral acid at temperatures between room temperature and about 50° C.

A ring contraction of the 14-membered lactone ring of the erythromycin framework in the compounds of the formula IV can be carried out in a known manner by intramolecular translactonization to give a 12-membered lactone ring with formation of the corresponding compounds of the formula II. To do this, the compounds of the formula IV are heated in a known manner in a lower alcohol in the presence of a base, for example at temperatures between 40° C. and 70° C., preferably the boiling point of the reaction mixture. Alkali metal carbonates are particularly suitable as bases, but organic bases such as tertiary amines, especially tertiary lower alkylamines, are also suitable. The configuration of the asymmetric centers does not change in this ring contraction.

The novel compounds of formula I and the physiologically acceptable acid addition salts thereof have interesting pharmacological properties, especially motilin-agonistic properties stimulating the motility of the gastrointestinal tract. They are free of antibiotic effects and have a high selective affinity for motilin receptors, whereas in dose ranges with motilin-agonistic efficacy they show virtually no relevant affinity for other receptors in the gastrointestinal tract such as adrenaline, acetylcholine, histamine, dopamine or serotonin receptors.

In the healthy state, the autonomic nervous system and hormones in the gastrointestinal tract cooperate to ensure controlled digestion of ingested food and in order to generate a controlled contraction activity of the gastrointestinal tract not only immediately after food intake but also when the gastrointestinal tract is empty. Motilin is a known gastrointestinal peptide hormone which stimulates the motility of the gastrointestinal tract and induces a coordinated motility throughout the gastrointestinal tract in the fasting state and after intake of food.

The compounds of the formula I show motilin-like physiological effects in that they act as agonists for motilin receptors. Thus, the compounds of the formula I show pronounced stimulating effects in the gastrointestinal region and at the lower esophagus sphincter. In particular, they bring about an increased rate of gastric emptying and a long-lasting increase in the resting tone of the esophagus sphincter. Because of their motilin-like profile of effects, the substances are useful for treating pathological states which are associated with motility disturbances in the gastrointestinal tract and/or reflux of chyme from the stomach into the esophagus. Thus, the compounds of the formula I are indicated, for example, for gastroparesis with a wide variety of causes, disturbances of gastric emptying and gastro-esophagal reflux, dyspepsia, abnormalities of colon motility as occur, for example, in irritable colon [=irritable bowel syndrome (IBS)] and postoperative motility disturbances, for example intestinal obstruction (ileus).

The gastrointestinally effective properties of the compounds of the formula I can be demonstrated in standard pharmacological test methods in vitro and in vivo.

Description of the Test Methods

1. Determination of the binding capacity of the test substances to motilin receptors.

The affinity of the compounds of the formula I for motilin receptors is measured in vitro on a fraction of a tissue homogenate from rabbit antrum. The displacement of radioactively labelled iodinated motilin from motilin receptor binding by the test substances is determined.

The receptor binding studies were carried out by a modification of the method of Borman et al. (Regulatory Peptides 15 (1986), 143–153). To prepare the $^{125}$iodine-labelled motilin, motilin is iodinated enzymatically using lactoperoxidase in a known manner, for example analogously to the method described by Bloom et al. (Scand. J. Gastroenterol. 11 (1976) 47–52).

To obtain the fraction of tissue homogenate used in the test from rabbit antrum, the antrum from which the mucosa has been removed is comminuted and homogenized in 10 times the volume of a cold homogenization buffer solution (50 mM tris-HCl buffer, 250 mM sucrose, 25 mM KCl, 10 mM $MgCl_2$, pH 7.4) with the addition of inhibitors (1 mM iodoacetamide, 1 μM pepstatin, 0.1 mM methylsulfonyl fluoride, 0.1 g/l trypsin inhibitor, 0.25 g/l bacitracin) with a homogenizer at 1500 revolutions per minute for 15 sec. The homogenizate is then centrifuged at 1000 g for 15 minutes, the resulting residue was washed four times with homogenization buffer solution and finally resuspended in 0.9% strength sodium chloride solution (in a volume corresponding to 5 times the amount by weight of the antrum). The tissue fraction obtained in this way, which is called "crude membrane preparation", was employed for the test.

For the binding test, 200 μl of the crude membrane fraction (0.5–1 mg of protein) in 400 μl of a buffer solution A (50 mM tris-HCl buffer, 1.5% BSA, 10 mM $MgCl_2$, pH 8.0) were incubated with 100 μl of iodinated motilin diluted in buffer solution B (10 mM tris-HCl buffer, 1% BSA, pH 8) (final concentration 50 pM) at 30° C. for 60 minutes. The reaction was stopped by adding 3.2 ml of cold buffer solution B, and bound and non-bound motilin were separated from one another by centrifugation (1000 g, 15 minutes). The residue obtained as pellet after the centrifugation was washed with buffer solution B and counted in a gamma counter. The displacement studies were carried out by adding increasing amounts of the substance to be tested to the incubation medium. The test substance solutions employed were aqueous solutions which are prepared by suitable dilution of $60 \times 10^{-4}$ molar aqueous stock solutions. Test substances which are sparingly soluble in water were initially dissolved in 60% strength ethanol, and this solution was diluted with sufficient water for the ethanol concentration in the solution to be tested not to exceed 1.6% by volume. The $IC_{50}$ of the particular test substance was determined from the resulting measured data as that concentration which brought about 50% inhibition of the specific binding of the iodinated motilin to the motilin receptors. From this the corresponding $pIC_{50}$ value was calculated. The $pIC_{50}$ value determined by the preceding method for the substance of Example 1 was 8.32.

2. In vivo determination of the effect of the substances on the rate of gastric emptying.

The determination of the rate of gastric emptying was carried out on beagle dogs which, before the test, had undergone surgical establishment of an esophagus fistula and implantation of a duodenal cannula. 15 minutes after duodenal administration of the test substances, the fasting conscious dogs were given 285 g of a semisolid caloric test meal through the esophagus fistula. The contents emptied from the stomach were collected through the duodenal cannula at 15-minute intervals. From the collected amounts of stomach contents, the time within which 50% emptying of the stomach takes place was calculated. The time is reported as measure of gastric emptying.

In this test model, the compound of Example 1 showed a distinct stimulation of gastric emptying at a dose of 0.46 μmole/kg. The time for 50% emptying of the stomach was reduced from 46 minutes in a control animal group to 27 minutes in animals which had received the test substance.

3. In vivo determination of the effect of the substances on the resting tone of the esophagus sphincter.

This determination is carried out on trained, conscious, fasting beagle dogs which, before the test, have each been given an esophagus fistula and a duodenal cannula. The pressure of the lower esophagus sphincter is measured by means of a perfused catheter system which has a lateral opening and which is connected to a pressure transducer and a recorder. The catheter is passed through the esophagus fistula into the stomach and then slowly withdrawn manually (=pull-through manometry). A peak is recorded when the catheter part with the lateral opening passes through the high-pressure zone of the lower esophagus sphincter. The pressure in mm Hg is determined from this peak.

In this way, initially the basal pressure of the esophagus sphincter is determined as control value. Subsequently, the test substance is administered intraduodenally and, after 15 minutes, the pressure at the lower esophagus sphincter is measured at 2-minute intervals for a period of 46 minutes. The increase in the pressure after administration of test substance compared with the previously determined basal pressure is calculated.

In this test, the basal tone of the esophagus sphincter was more than doubled by a dose of 0.251 μmole/kg of the compound of Example 1. This effect persisted throughout the 45 minute duration of the test.

Because of their effects in the gastrointestinal tract, the compounds of formula I are useful in gastroenterology as pharmaceuticals for larger mammals, especially humans, for the prophylaxis and treatment of motility disturbances in the gastrointestinal tract.

The doses to be used may differ between individuals and naturally vary depending on the nature of the condition to be treated and the administration form. For example, parenteral formulations will generally contain less active substance than oral products. However, in general drug forms with an active substance content of 5 to 200 mg per single dose are suitable for administrations to larger mammals, especially humans.

As medicinal agents, the compounds of the formula I can be contained with conventional pharmaceutical auxiliary substances in pharmaceutical formulations such as, for example, tablets, capsules, suppositories or solutions. These pharmaceutical formulations can be produced by known methods using conventional solid vehicles such as, for example, lactose, starch or talc or liquid diluents such as, for example, water, fatty oils or liquid paraffins and using customary pharmaceutical auxiliary substances, for example tablet disintegrating agents, solubilizers or preservatives.

The following examples are intended to illustrate the invention in further detail without limiting its scope in any way.

Example 1

[2R,3R(2R',3R'),6R,7S,8S,9R,10R]-3-(2',3'-dihydroxypent-2'-yl)-7-[(2,6-dideoxy-3-C-methyl-3-0-methyl-α-L-ribo-hexopyranosyl)-oxy]-9-[(3,4,6-trideoxy-3-(N-methyl-N-isopropylamino)-β-D-xylo-hexopyranosyl)-oxy]-2,6,8,10,12-pentamethyl-4,13-dioxabicyclo[8.2.1]-tridec-12-en-5-one (=compound of the formula I, $R^1$=methyl).

A) Preparation of N-demethylerythromycin A 20 g of erythromycin A (=27.2 mmole) and 11.2 g (=136.2 mmole) of sodium acetate were dissolved in 200 ml of an 8:2 methanol/water mixture. The solution was heated to 47° C. Then 6.9 g (=136.2 mmole) of iodine were added. The pH was kept at 8 to 9 by adding dilute aqueous sodium hydroxide solution. After 3 hours, the reaction mixture was worked up by pouring it into a mixture of 1 liter of water and 20 ml of ammonium hydroxide solution. The reaction mixture was extracted with ethyl acetate, and the organic extract was washed with ammonium hydroxide-containing water and concentrated. The crude product remaining after removal of the solvent was recrystallized from acetone/ammonium hydroxide solution 50:3. Melting point 143°–148° C.

B) Preparation of N-demethyl-8,9-anhydroerythromycin A 6,9-hemiketal (=compound of the formula IV, $R^1$=methyl).

21 g of the product obtained in A) were dissolved in 110 ml of glacial acetic acid, and the solution was stirred at room temperature for 1 hour. The reaction mixture was then worked up by adding it dropwise to 400 ml of concentrated ammonium hydroxide solution cooled in ice. The reaction mixture was extracted with ethyl acetate, the organic extract was washed with water, and the solvent was stripped off. The crude product remaining as residue was recrystallized first from ether and then from methanol. 14 g of pure product with a melting point of 145° C. were obtained.

C) Preparation of [2R,3R(2R',3R'),6R,7S,8S,9R,10R]-3-(2',3'-dihydroxypent-2'-yl)-7-[(2,6-dideoxy-3-C-methyl-3-0-methyl-α-L-ribo-hexopyranosyl)-oxy]-9-[(3,4,6-trideoxy-3-methylamino-β-D-xylo-hexopyranosyl)-oxy]-2,6,8,10,12-pentamethyl-4,13-dioxabicyclo[8.2.1]tridec-12-en-5-one (=compound of the formula II, $R^1$=methyl).

9.4 g (=13.4 mmole) of the product obtained in B) were boiled under reflux with 1.9 g (=13.4 mmole) of potassium carbonate in methanol for 2.5 hours. The reaction mixture was worked up by concentrating it, diluting with water and extracting with ethyl acetate. The crude product remaining after removal of the solvent was recrystallized from isopropanol. 7.1 g of pure product with a melting point of 199° to 200° C. were obtained, optical rotation $[\alpha]_D^{20}$: −31.6° (c =1, methanol).

D) Preparation of the title compound.

2 g (=2.8 mmole) of the product obtained in C) above were dissolved in methanol, and the pH of the solution was adjusted to pH 4 by adding dilute hydrochloric acid solution. To the solution were added 2 g of a molecular sieve (calcium aluminium silicate, pore diameter 4 Å), an excess of acetone and 0.4 g (=6.4 mmole) of sodium cyanoborohydride. The reaction mixture was stirred for 12 hours. To work up the reaction mixture, the molecular sieve was filtered out, the filtrate was concentrated, mixed with water and extracted with ethyl acetate. The crude product remaining as a residue after concentration of the ethyl acetate extract was purified by column chromatography on silica gel (eluent ethyl acetate/methanol 95:5). 1.4 g of the title compound with a melting point of 130° to 134° C. were obtained, optical rotation $[\alpha]_D^{20}$: −32.8°.

Example 2

[2R,3R(2R',3R'),6R,7S,8S,9R,10R]-3-(2',3'-dihydroxypent-2'-yl)-7-[(2,6-dideoxy-3-C-methyl-3-0-methyl-α-L-ribo-hexopyranosyl)-oxy]-9-[(3,4,6-trideoxy-3-(N-methyl-N-isopropylamino)-β-D-xylo -hexopyranosyl)-oxy]-2,6,8,10,12-pentamethyl-4,13-dioxabicyclo[8.2.1]-tridec-12-en-5-one (=compound of the formula I, $R^1$=methyl).

A) Preparation of N-demethylerythromycin A.

5 g of erythromycin A and 4.7 g of sodium acetate (×3 H₂O) were dissolved in 200 ml of an 8:2 methanol/water mixture. 1.75 g of iodine were added to the solution, and the reaction mixture was then irradiated with a quartz lamp at room temperature for 20 minutes. Subsequently, half the solvent was evaporated, and the remaining reaction mixture was poured into a mixture of 140 ml of water and 10 ml of ammonia. The reaction mixture was extracted three times with 20 ml portions of methyl t-butyl ether. The ether extract was separated and some of the ether was evaporated. The reaction product was then left to crystallize out and was recrystallized from acetone. 2 g of N-demethylerythromycin A were obtained.

B) To prepare N-demethyl-8,9-anhydroerythromycin A 6,9-hemiketal (=compound of the formula IV, $R^1$=methyl), 2 g of the product obtained in A) were treated as described in Example 1 B). 2.3 g of the hemiketal were obtained as an amorphous solid.

C) To prepare [2R,3R(2R',3R'),6R,7S,8S,9R,10R]-3-(2',3'-dihydroxypent-2'-yl)-7-[(2,6-dideoxy-3-C-methyl-3-0-methyl-α-L-ribo-hexopyranosyl)-oxy]-9-[(3,4,6-trideoxy-3-methylamino-β-D-xylo -hexopyranosyl)-oxy]-2,6,8,10,12-pentamethyl-4,13-dioxabicyclo[8.2.1]-tridec-12-en-5-one (=compound of the formula II, $R^1$=methyl), 2.3 g of the product obtained above were treated as described in Example 1 C). The resulting crude product was recrystallized from ethyl acetate. 1.3 g of pure product with a melting point of 199°–202° C. were obtained.

D) 1.3 g of the product obtained above were added to a mixture of 26 ml of acetone and 0.11 ml of acetic acid. 0.6 g of sodium triacetoxyborohydride was added in portions under a nitrogen atmosphere to the reaction mixture, and the reaction mixture was stirred at room temperature for 4 hours. Then two thirds of the solvent were evaporated, and the residue was diluted with 40 ml of ethyl acetate. While stirring vigorously, 65 ml of a saturated sodium bicarbonate solution were added. The organic phase was separated from the clear solution which formed, and the aqueous phase was washed once more with 20 ml of ethyl acetate. The combined organic phases were washed with 13 ml of water and dried over sodium sulfate. The solvent was evaporated, the residue was taken up in 20 ml of toluene, and the toluene was then evaporated. The resulting crude product was purified by filtration through an aluminium oxide column (25 g of Al₂O₃, activity level II/III) using ethyl acetate as eluent. The solvent was then evaporated, and the residue was dissolved in boiling ethyl acetate. Subsequently, n-hexane was added until the mixture became cloudy. The product was left to crystallize out in the cold. The crystals which formed were filtered out under reduced pressure and washed with n-hexane. 0.8 g of the title compound with a melting point of 128°–135° C. was obtained.

E) To convert the title compound into its acetate, 1 g (=1.3 mmole) of it was dissolved in methanol, and 0.08 ml (=1.3 mmole) of glacial acetic acid was added to the solution. The solvent was subsequently stripped off under reduced pressure, and the acetate of the title compound which had formed was dried. Melting point of the acetate of the title compound: 145°–150° C. Optical rotation $[\alpha]_D^{20}$: −30.8° (c=1, methanol).

Example I

Tablets having the following composition per tablet were produced:

| | |
|---|---|
| [2R,3R(2R′,3R′),6R,7S,8S,9R,10R]-3-(2′,3′-Dihydroxypent-2′-yl)-7-[(2,6-dideoxy-3-C-methyl-3-0-methyl-α-L-ribo-hexopyranosyl)-oxy]-9-[(3,4,6-trideoxy-3-(N-methyl-N-isopropyl-amino)-β-D-xylo-hexopyranosyl)-oxy]-2,6,8,10,12-pentamethyl-4,13-dioxabicyclo[8.2.1]tridec-12-en-5-one (= compound of the formula I, $R^1$ = methyl) | 20 mg |
| Maize starch | 60 mg |
| Lactose | 135 mg |
| Gelatin (as 10% strength solution) | 6 mg |

The active compound, the maize starch and the lactose were made into a paste with the 10% strength gelatin solution. The paste was comminuted, and the resulting granules were placed on a suitable metal sheet and dried at 45° C. The dried granules were passed through a comminuting machine and mixed with the following other auxiliary substances in a mixer:

| | |
|---|---|
| Talc | 5 mg |
| Magnesium stearate | 5 mg |

| -continued | |
|---|---|
| Maize starch | 9 mg | and then compressed to 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A [2R,3R(2R′,3R′),6R,7S,8S,9R,10R]-3-(2′,3′-dihydroxypent-2′-yl)-2,6,8,10,12-pentamethyl-4,13-dioxabicyclo[8.2.1]tridec-12-en-5-one compound corresponding to the formula I:

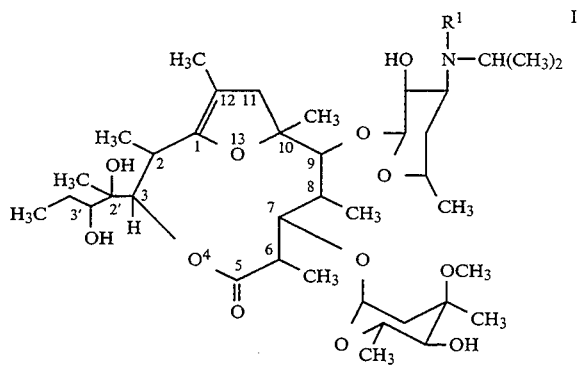

in which $R^1$ denotes methyl, or a stable and physiologically acceptable acid addition salt thereof.

2. A pharmaceutical composition comprising an effective gastrointestinal motility affecting amount of a compound according to claim 1, and at least one pharmaceutically acceptable adjuvant or carrier.

* * * * *